US006210692B1

(12) United States Patent
Lorant

(10) Patent No.: US 6,210,692 B1
(45) Date of Patent: Apr. 3, 2001

(54) EMULSION COMPRISING A HYDROPHILIC THICKENING COMPOUND AND A POLYSACCHARIDE ALKYL ETHER, COMPOSITIONS AND PRODUCTS COMPRISING THE EMULSION, AND USES THEREOF

(75) Inventor: Raluca Lorant, Thiais (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/397,343

(22) Filed: Sep. 15, 1999

(30) Foreign Application Priority Data

Aug. 16, 1998 (FR) .................................................. 98 11576

(51) Int. Cl.$^7$ ............................ A61K 7/00; A61K 7/025; A61K 7/06
(52) U.S. Cl. ............................ 424/401; 424/64; 424/70.1; 424/70.7
(58) Field of Search ............................ 424/401, 64, 70.1, 424/70.7

(56) References Cited

U.S. PATENT DOCUMENTS

| 5,318,995 | 6/1994 | Mondet et al. | 514/772.1 |
| 5,736,125 | 4/1998 | Morawsky et al. | 424/59 |
| 5,961,998 * | 10/1999 | Arnaud et al. | 424/401 |

FOREIGN PATENT DOCUMENTS

| 0 268 164 | 5/1988 | (EP) . |
| 0 281 360 | 9/1988 | (EP) . |
| 0 406 042 | 1/1991 | (EP) . |
| 0 412 705 | 2/1991 | (EP) . |
| 0 482 417 | 4/1992 | (EP) . |
| 0 708 114 | 4/1996 | (EP) . |
| 0 795 321 | 9/1997 | (EP) . |
| 0 795 322 | 9/1997 | (EP) . |
| 0 795 323 | 9/1997 | (EP) . |
| 0 815 844 | 1/1998 | (EP) . |
| 0 832 645 | 4/1998 | (EP) . |
| WO 96/37180 | 11/1996 | (WO) . |

OTHER PUBLICATIONS

T.G. Majewicz et al., "Oil–Based Cosmetic and Therapueitc Compositions Containing Ethylguar", Research Disclosure, Oct. 1995, p. 642.
English language Derwent Abstract of EP 0 795 321.
English language Derwent Abstract of EP 0 795 322.
English language Derwent Abstract of EP 0 795 323.
English language Derwent Abstract of EP 0 815 844.
English language Derwent Abstract of EP 0 832 645.

* cited by examiner

Primary Examiner—Shelley A. Dodson
Assistant Examiner—Konata M. George
(74) Attorney, Agent, or Firm—Finnegan, Henderson, Farabow, Garrett & Dunner, L.L.P.

(57) ABSTRACT

An emulsion comprising an aqueous phase and an oily phase and additionally comprising a hydrophilic thickening compound and a polysaccharide alkyl ether, as well as a cosmetic or dermatological composition comprising such an emulsion. The use of such a combination makes it possible to stabilize an emulsion, in particular an oil-in-water emulsion and more particularly an emulsion not comprising a surfactant.

52 Claims, No Drawings

EMULSION COMPRISING A HYDROPHILIC THICKENING COMPOUND AND A POLYSACCHARIDE ALKYL ETHER, COMPOSITIONS AND PRODUCTS COMPRISING THE EMULSION, AND USES THEREOF

The present invention relates to a composition which is provided in the form of an emulsion capable of being used in the cosmetics and dermatological fields, in particular for caring for or treating the skin of the body or of the face, more particularly for caring for or treating dry or sensitive skin. The invention also relates to a cosmetic or dermatological composition comprising such an emulsion.

Current cosmetic or dermatological compositions are generally provided in the form of an emulsion of the oil-in-water type (that is to say, a vehicle composed of a continuous aqueous dispersing phase and of a non-continuous oily disperse phase) or of an emulsion of the water-in-oil type (that is to say, a vehicle composed of a continuous fatty dispersing phase and of a non-continuous aqueous disperse phase).

Water-in-oil emulsions therefore comprise a continuous oily phase and make possible the formation, at the surface of the skin, of a lipid film which prevents transepidermal water loss and protects the skin from external attacks. These emulsions are particularly appropriate for protecting and nourishing the skin and in particular for treating dry skin.

Oil-in-water emulsions, for their part, contribute to the skin, on application, a softer, less greasy and lighter feel than water-in-oil emulsions.

Emulsions are generally stabilized by incorporation of emulsifying surfactants of the oil-in-water (O/W) type or of the water-in-oil (W/O) type which, by virtue of their amphiphilic structure, become positioned at the oil/water interface and thus stabilize the dispersed droplets. It is generally necessary to introduce these surfactants in a large amount, which can range up to 10% by weight with respect to the total weight of the emulsion, in order to obtain adequate stability.

In point of fact, these amphiphilic surfactants, used in large amounts, can prove to be irritating to the skin, eyes and/or scalp of the user. Furthermore, their presence at high concentrations can result in non-cosmetic effects, such as a rough, clinging and/or sticky feel, or a compact and heavy final composition. Furthermore, the surfactants must be chosen according to the polarity of the oils and are therefore only compatible with a limited number of oils, thus limiting the variety of the formulations.

Formulators of emulsions are constantly seeking to reduce the content of surfactant in order to improve the harmlessness of the emulsions with regard to the skin, eyes and/or scalp and to improve their cosmetic properties. The main difficulty with which they are generally confronted is to obtain stable emulsions.

Application WO 96/37180 has thus provided a composition capable of applications in the pharmaceutical and/or cosmetics fields which is provided in the form of a "pseudoemulsion" and is devoid of surfactant. The composition comprises, on the one hand, in the aqueous phase, a gelling agent chosen in particular from polyoses or acrylic polymers and, on the other hand, in the fatty phase, a consistency factor chosen from waxy fatty substances and in particular glycerol esters. The consistency factor present in the fatty phase is a substance which is semisolid at 25° C. and has a melting point of greater than 50° C.; it is dissolved under warm conditions in the fatty phase and then recovers its starting semisolid consistency under cold conditions, conferring a degree of consistency and a degree of viscosity on the fatty phase. The composition thus obtained exhibits a microscopic structure different from that of an emulsion.

However, it has been found that, beyond a certain amount of fatty phase, the pseudoemulsion loses stability, under warm conditions and/or over time. This is particularly true for levels of fatty phase of greater than 20% by weight with respect to the total weight of the pseudoemulsion. In point of fact, a high level of fatty phase in an O/W emulsion can prove to be highly advantageous, in particular for cosmetic compositions intended for the care of dry skin. Furthermore, the cosmetic properties of this pseudoemulsion are inadequate: its texture is heterogeneous, its feel greasy, and uptake with the finger is found to be poor.

There, therefore, still remains the need to have available an O/W emulsion which is stable over time, although it does not comprise a surfactant, and which can comprise a large amount of fatty phase without losing its stability.

The aim of the present invention is to alleviate this need and to provide an emulsion, in particular an O/W emulsion, which can avoid the disadvantages mentioned above and which can be stable while comprising a reduced amount of surfactant and which can tolerate a large amount of fatty phase.

The inventor has found, surprisingly, that it is possible to obtain an emulsion having good cosmetic properties and good stability by using a specific combination of thickeners of the oily phase and of the aqueous phase.

The subject-matter of the present invention is therefore an emulsion comprising an aqueous phase and a fatty phase, additionally comprising at least one hydrophilic thickening compound, at least one polysaccharide alkyl ether formed of two units comprising at least two different oside rings, each unit comprising at least one hydroxyl group substituted by a saturated hydrocarbon-comprising alkyl chain, and at least one solvent medium for the polysaccharide alkyl ether.

Another subject-matter of the invention is a cosmetic or dermatological composition comprising, in a cosmetically or dermatologically acceptable medium, such an emulsion.

A further subject-matter of the invention is the use of such an emulsion for the cosmetic treatment of the skin, hair, eyelashes, eyebrows, nails, mucous membranes or scalp; in particular, for caring for the face and/or body, making up the face and/or body, removing make-up; or antisun protection; and/or in the manufacture of a dermatological composition intended for the treatment of the skin, hair, eyelashes, eyebrows, nails, scalp and/or mucous membranes.

Another subject-matter of the invention is a process for the nontherapeutic treatment of the skin, in particular dry and/or sensitive skin, hair, eyelashes, eyebrows, nails, mucous membranes or scalp which comprises applying, to the substrate, an emulsion as defined above.

A further subject-matter of the invention is the use of a hydrophilic thickening compound and of a polysaccharide alkyl ether as defined above for stabilizing an emulsion comprising at least one solvent medium for the polysaccharide alkyl ether, in particular an oil-in-water emulsion and preferably an emulsion not comprising surfactant.

It has been found that the emulsion obtained according to the invention remains stable over time at room temperature or at higher temperatures, despite the low amount, indeed even the absence, of surfactant.

Furthermore, in the case of an oil-in-water emulsion, the fatty phase is completely dispersed in the aqueous phase and makes it possible to obtain a homogeneous composition having the microscopic structure of an emulsion.

The emulsion obtained is easy to apply to the skin, mucous membranes, scalp, hair, eyelashes, eyebrows or nails.

The textures obtained are particularly original: the emulsions are creamy and smooth and are entirely free from the gelled, indeed even gelatinous, appearance of some emulsions of the prior art, the external aqueous phase of which is gelled.

The cosmetic feel on the skin is also appreciated: on application, the emulsion provides a feeling of freshness and of comfort while being rich and nourishing; it is soft and comfortable and not in any way clinging.

The emulsion thus obtained is particularly suited to caring for and treating dry and/or sensitive skin, through the possibility of the presence of a large amount of fatty substance contributing care and comfort and through the absence of irritating surfactant.

Furthermore, in the case of an oil-in-water emulsion, the emulsions according to the invention do not require an onerous and expensive procedure, such as a high-pressure homogenization, but can be prepared according to a conventional procedure.

The emulsion according to the invention is preferably provided in the form of an oil-in-water emulsion comprising an internal fatty or oily phase dispersed in an external aqueous phase.

The aqueous phase can comprise, preferably, water and/or a thermal water and/or a spring water and/or a mineral water and/or a floral water.

The emulsion furthermore comprises at least one hydrophilic thickening compound which can be chosen from any hydrophilic thickener known to a person skilled in the art. Mention may in particular be made of the following compounds:

synthetic polymers, polysaccharide biopolymers, such as xanthan gum, locust bean gum, guar gum, alginates or modified celluloses, such as hydroxyethylcellulose, methylcellulose, hydroxypropylcellulose and carboxymethylcellulose, aluminium magnesium silicate;

inorganic thickeners, such as smectites or hectorites, whether modified or unmodified (Bentone or Laponite, for example), their mixtures.

Mention may be made, among synthetic polymers, of:

(A) polyacrylic acids and in particular:
  (i) poly(glyceryl(meth)acrylate) polymers, such as Hispagel or Lubragel from the companies Hispano Quimica or Guardian,
  (ii) optionally crosslinked acrylic acid homopolymers and copolymers or one of their salts, such as those sold under the name "Carbopol" by the company Goodrich;

(B) polyacrylamide-based polymers and in particular:
  (i) the product sold under the name Sepigel 305 by Seppic, which is composed of an O/W emulsion comprising 35–45% by weight of crosslinked neutralized acrylamide/2-acrylamido-2-methyl-propanesulphonic acid copolymer, 15–25% by weight of isoparaffin hydrocarbons, 3–8% by weight of polyethylene glycol 7EO lauryl ether, and water;
  (ii) acrylate/octylacrylamide copolymers, such as Dermacryl from National Starch;
  (iii) crosslinked polymers of acrylamide and of methacryloyloxyethyltrimethylammonium chloride, such as Salcare SC92 from Allied Colloids;
  (iv) crosslinked polymers of acrylamide and of ammonium acrylate, such as PAS 5161 or Bozepol C from Hoechst;
  (v) crosslinked and virtually or completely neutralized poly(2-acrylamido-2-methylpropane-sulphonic acid) polymers.

(C) copolymers composed of a major fraction of monomeric units originating from monomers chosen from mono-olefinically unsaturated $C_3$–$C_6$ carboxylic acid monomers and their anhydrides and of a minor fraction of monomeric units originating from monomers chosen from esters with a fatty chain of acrylic acid monomers, these copolymers optionally being crosslinked.

The crosslinked and virtually or completely neutralized poly(2-acrylamido-2-methylpropanesulphonic acid) polymers which can be used in the context of the invention are water-soluble or swellable in water. They are generally characterized in that they comprise, distributed randomly:

a) from 90 to 99.9% by weight of units of the following formula (1):

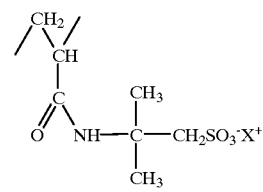

(1)

in which $X^+$ is chosen from at least one cation, at most 10 mol % of the $X^+$ cations being able to be $H^+$ protons;

b) from 0.01 to 10% by weight of crosslinking units originating from at least one monomer having at least two olefinic double bonds; the proportions by weight being defined with respect to the total weight of the polymer.

They preferably comprise from 98 to 99.5% by weight of units of formula (1) and from 0.2 to 2% by weight of crosslinking units.

$X^+$ is chosen from at least one cation, the at least one cation being chosen from a proton, an alkali metal cations, alkaline earth metal cations, and the ammonium ion. More particularly, 90 to 100 mol % of the cations are $NH_4^+$ cations and 0 to 10 mol % are protons ($H^+$).

The crosslinking monomers having at least two olefinic double bonds preferably are chosen from dipropylene glycol diallyl ether, polyglycol diallyl ethers, triethylene glycol divinyl ether, hydroquinone diallyl ether, tetraallyloxyethane or other polyfunctional alcohol allyl or vinyl ethers, tetraethylene glycol diacrylate, triallylamine, trimethylolpropane diallyl ether, methylenebisacrylamide or divinylbenzene.

The crosslinking monomers having at least two olefinic double bonds are more particularly chosen from those corresponding to the following general formula (2):

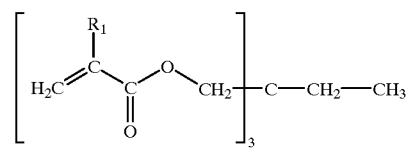

(2)

in which $R_1$ is chosen from a hydrogen atom and $C_1$–$C_4$ alkyls and more particularly methyl (trimethylolpropane triacrylate).

These crosslinked polymers can be chosen from those exhibiting a viscosity, measured with a Brookfield viscometer, rotor 4, at a rotational speed of 100 revolutions/minute in a 2% solution in water at 25° C., of greater than or equal to 1000 centipoises, in another embodiment, of a viscosity ranging from 5000 to 40,000 centipoises and yet in another embodiment, of a viscosity more particularly from 6500 to 35,000 centipoises.

These polymers are disclosed in particular in Application EP 815,844, the contents of which are explicitly incorporated herein by reference.

It should be noted that this Application EP 815,844 relates to a cosmetic or dermatological composition in the form of an oil-in-water emulsion which is stable while not comprising surfactant and which furthermore comprises a crosslinked poly(2-acrylamido-2-methyl-propanesulphonic acid) polymer neutralized to at least 90%. This polymer is added to the aqueous phase, which it thickens. However, in the composition thus obtained, the fatty phase can only represent up to approximately 12–15% by weight of the emulsion. Beyond this amount of fatty phase, the composition loses stability.

The optionally crosslinked copolymers composed of a major fraction of monomeric units originating from monomers chosen from mono-olefinically unsaturated $C_3$–$C_6$ carboxylic acid and their anhydrides and of a minor fraction of monomeric units originating from monomers chosen from esters with a fatty chain of acrylic acid monomers which can be used in the context of the present invention can be prepared by polymerizing a predominant amount of mono-olefinically unsaturated carboxylic monomer or of its anhydride with a smaller amount of acrylic ester with a fatty chain monomer. The amount of carboxylic monomer or of its anhydride is preferably between 80 and 98%, inclusive, by weight and more particularly between 90 and 98%, inclusive, by weight; the acrylic ester is preferably present in amounts of between 2 and 20%, inclusive, by weight and more particularly between 2 and 10%, inclusive, by weight; the percentages are calculated with respect to the weight of the two monomers.

The preferred carboxylic monomers are chosen from those corresponding to the formula: $CH_2$=CR—COOH, in which R is chosen from a hydrogen, halogens, a hydroxyl, a lactone group, a lactam group, a cyanogen group (—CN), monovalent alkyl groups, aryl groups, alkylaryl groups, aralkyl groups and cycloaliphatic groups.

The particularly preferred carboxylic monomers are chosen from acrylic acid, methacrylic acid, maleic anhydride and their mixtures.

The acrylic ester with a fatty chain monomers are preferably chosen from those corresponding to the formula: $CH_2$=$CR^1$—$COOR^2$, in which $R^1$ is chosen from a hydrogen, a methyl and an ethyl, and $R^2$ is chosen from $C_8$–$C_{30}$ alkyl groups, $C_8$–$C_{30}$ oxyalkylene groups and carbonyl($C_8$–$C_{30}$ oxyalkylene) groups.

The particularly preferred ester monomers are those in which $R^1$ is chosen from a hydrogen or a methyl and those in which $R^2$ is chosen from $C_{10}$–$C_{22}$ alkyl groups. Mention may in particular be made of decyl, lauryl, stearyl, behenyl or melissyl acrylates and methacrylates.

Some of these copolymers are disclosed in particular in Application EP-A-0,268,164, the disclosure of which is specifically incorporated by reference herein, and are obtained according to the preparation methods disclosed in this same document.

Mention may more particularly be made of the copolymers sold under the name Pemulen by the Company Goodrich and in particular the acrylate/$C_{10}$–$C_{30}$ alkyl acrylate copolymer, such as the product Pemulen TR 2.

In the context of the present invention, use may very clearly be made of a mixture of several hydrophilic thickeners as defined above.

The hydrophilic thickeners can be present in the cosmetic or dermatological compositions of the invention in concentrations generally ranging from 0.05 to 10% by weight with respect to the total weight of the composition and, in another embodiment, from 0.5 to 4% by weight.

The viscosity of the aqueous phase is generally of the order of 30,000 to 80,000 centipoises (30–80 Pa.s), measured with a Brookfield viscometer, needle 7, at a speed of 20 revolutions/minute.

The emulsion according to the invention furthermore comprises an oily phase which comprises at least one polysaccharide alkyl ether formed of two units comprising at least two different oside rings, each unit comprising at least one hydroxyl group substituted by a saturated hydrocarbon-comprising alkyl chain.

The term "hydrocarbon-comprising alkyl chain" is understood to mean a linear or branched chain comprising from 1 to 24, alternatively from 1 to 10, further alternatively from 1 to 6 and finally from 1 to 3 carbon atoms. In particular, the alkyl chain is chosen from saturated chains and in particular methyl, ethyl, n-propyl, isopropyl, n-butyl, isobutyl, tert-butyl or n-pentyl.

The oside rings are chosen in particular from mannose, galactose, glucose, furanose, rhamnose or arabinose.

These alkyl ethers can be manufactured as disclosed in the documents EP-A-281,360, EP-A-708,114 or EP-A-281,360, the disclosure of each of which is explicitly incorporated herein by reference.

The polysaccharide alkyl ether preferably has a weight-average molecular weight of greater than 100,000 and preferably of greater than 200,000. This molecular weight can range up to 1 million. This alkyl ether can comprise from one to six and better still from two to four hydroxyl groups per unit which are substituted by a saturated or unsaturated hydrocarbon-comprising alkyl chain.

According to a preferred embodiment of the invention, the polysaccharide alkyl ether is an alkyl ether of a gum and more particularly of a gum which is nonionic overall, that is to say comprising few or no ionic groups.

Mention may be made, as appropriate gums, of, for example, guar gum, the unit of which comprises a galactose and a mannose; locust bean gum, the unit of which comprises a galactose and a mannose; karaya gum, which is a complex mixture of rhamnose, galactose and galacturonic acid; or gum tragacanth, which is a complex mixture of arabinose, galactose and galacturonic acid.

The polysaccharide alkyl ether is preferably a derivative of guar gum. Thus, the alkyl ether is advantageously an alkylated galactomannan with a $C_1$ to $C_6$ and better still $C_1$ to $C_3$ alkyl chain and more particularly the ethylated guar having a degree of substitution of 2 to 3 and in particular of approximately 2.5 to 2.9, as disclosed in the documents RD 95378007 (October 1995) and EP-A-708,114. Mention may be made, among commercial products, of the gums sold by the company Aqualon under the names N-Hance-AG 200® and N-Hance-AG 50®.

In the context of the present invention, use may very obviously be made of a mixture of several polysaccharide alkyl ethers as defined above.

The polysaccharide alkyl ethers can be present in the emulsions and/or compositions according to the invention in concentrations preferably ranging from 0.1 to 10% by weight with respect to the total weight of the composition and more preferably from 0.5 to 2% by weight.

The polysaccharide alkyl ether can advantageously be present in an amount such that the ratio (by weight) of the amount of oil to the amount of polysaccharide alkyl ether is chosen within the range from 5 to 1000.

The viscosity of the oily phase is preferably of the order of 6000 to 20,000 centipoises (6–20 Pa.s), measured with a Brookfield viscometer, needle 5, at a speed of 20 revolutions/minute.

The liquid fatty phase of the emulsion according to the invention comprises at least one solvent medium for the polysaccharide alkyl ether which can be an oil. The term "oil" is understood to mean any fatty substance which is liquid at room temperature (25° C.).

Mention may be made, among oils which can be used as solvent medium for the polysaccharide alkyl ether according to the invention, of, for example:

oils of vegetable origin, such as liquid triglycerides, for example sunflower, maize, soybean, jojoba, cucumber, grape seed, sesame, hazelnut, apricot, macadamia or castor oil; or triglycerides of caprylic/capric acids, such as those sold by the company Stéarineries Dubois or those sold under the names Miglyol 810, 812 and 818® by the company Dynamit Nobel, oils of animal origin, such as lanolin, oils of mineral origin, synthetic oils, such as fatty alcohols, for example 2-octyldodecanol; esters and in particular fatty acid esters and especially esters having a total number of carbon atoms chosen between 12 and 80, preferably between 16 and 50; or phenylated silicones and in particular phenyl trimethicones, diphenyl dimethicones or polymethylphenylsiloxanes.

A person skilled in the art knows, on the basis of his knowledge, how to determine, by simple routine tests, the solvating oils for the polysaccharide alkyl ether.

Supplementary oils which are nonsolvating for the polysaccharide alkyl ether can additionally be added to the oily phase of the emulsion. Mention may in particular be made, as supplementary oil, of silicone resins and gums which are liquid at room temperature, partially fluorinated hydrocarbon-comprising oils, perfluorinated oils, silicone oils which are devoid of aromatic groups, such as linear or branched polysiloxanes, for example polydimethylpolysiloxanes, polyethylmethylpolysiloxanes or polyalkylmethylsiloxanes, and cyclic polysiloxanes, such as octamethylcyclotetrasiloxane, decamethylcyclopentasiloxane or their mixtures; fluorinated silicone oils; polysiloxanes functionalized by one or more hydroxyl functional groups and/or one or more polyether groups, such as dimethicone copolyols; or linear or branched hydrocarbons, such as liquid petrolatum, isohexadecane or isododecane.

The solvating oils for the polysaccharide alkyl ether can represent 15 to 99.9% by weight of the total weight of the oily phase of the emulsion, preferably 75 to 95%. The supplementary oils can be added in an amount which can range from 0 to 75% by weight with respect to the total weight of the oily phase, preferably from 0 to 50% by weight.

The emulsion according to the invention can comprise 1 to 50% by weight of fatty phase, preferably 5 to 30% by weight and more preferably 10 to 20% by weight of fatty phase.

In a known way, the emulsion according to the invention can optionally comprise a small amount of a surfactant, in particular an O/W surfactant, although this is not necessary to obtain a stable emulsion. The amount of surfactant can represent from 0.1 to 3% and preferably from 0.1 to 2% of the total weight of the emulsion. Advantageously, the emulsion does not comprise surfactant.

The emulsion according to the invention can be used in particular in the cosmetics and/or dermatological fields. It can be used as is and thus itself constitute a cosmetic or dermatological composition; it can also be incorporated in a more sophisticated cosmetic or dermatological composition.

The compositions according to the invention, composed of or comprising the emulsion, comprise a cosmetically or dermatologically acceptable medium, that is to say a medium compatible with all keratinous substances, such as the skin, nails, mucous membranes and hair or any other cutaneous region of the body. This medium can comprise, in a way known per se, the constituents conventionally employed in the field of application under consideration.

In particular, these compositions can comprise:

waxes chosen from animal, fossil, vegetable, mineral or synthetic waxes known per se, such as paraffin waxes, polyethylene waxes, carnauba or candelilla waxes, beeswaxes, microcrystalline wax or silicone waxes;

hydrophilic or lipophilic cosmetic and/or dermatological active principles, such as softeners, antioxidants, opacifiers, emollients, hydroxy acids, antifoaming agents, moisturizers, vitamins, fragrances, preservatives, dyes, sequestering agents, polymers, propellants, basifying or acidifying agents, UV screening agents, ceramides, agents for combating free radicals, slimming agents, bactericides, antidandruff agents, complexing agents or odour absorbers;

pulverulent materials, such as fillers, pigments and/or pearlescent agents. These adjuvants, depending on their nature, can be introduced into the fatty phase or into the aqueous phase. Of course, a person skilled in the art will take care to choose this or these optional additional compounds and/or their amount so that the advantageous properties of the composition according to the invention are not, or not substantially, detrimentally affected by the envisaged addition.

The emulsion and the composition according to the invention can be prepared according to techniques known to a person skilled in the art.

In particular, the emulsion can be prepared by dissolving the polysaccharide alkyl ether in the oily phase heated to 60–80° C., by then dissolving the hydrophilic thickener in the aqueous phase heated to 60–80° C., and by dispersing the fatty phase in the aqueous phase with stirring.

The compositions according to the invention can be provided in the form of a suspension or a dispersion in the fatty substances; in the form of a nonionic vesicular dispersion; in the form of a simple or complex emulsion (O/W, W/O, O/W/O or W/O/W), preferably of oil-in-water type; a cream, a milk, a gel, an ointment, an aerosol foam or a spray; a serum or a paste.

They find an application in particular in a great number of cosmetic or dermatological treatments of the skin, hair, eyelashes, eyebrows, nails, mucous membranes or scalp; mention may in particular be made of caring for the face and/or body (protection, treatment or care creams for the face, for the hands or for the body; protection or care body milks; or lotions, gels or foams for caring for the skin and mucous membranes or for cleansing the skin); making up the face and/or body (lipstick, eyeliner, foundation, mascara, concealer, eye shadow or face powder); removing make-up; antisun protection; or the dermatological treatment of diseases of the skin, hair, eyelashes, eyebrows, nails, scalp and/or mucous membranes.

They find a preferred application in cosmetic or dermatological compositions intended for dry and/or sensitive skin.

The invention is illustrated in more detail in the following examples, in which the % are given by weight.

EXAMPLE 1
Smoothing Eye-contour Cream

| Phase A | |
|---|---|
| Crosslinked poly(2-acrylamido-2-methyl-propanesulphonic acid) (Example A of EP 815,844), at 2% in water | 1% |
| Glycerol | 5% |
| Preservatives | 0.3% |
| Water | q.s. for 100% |
| Phase B | |
| Sesame oil | 10% |
| Castor oil | 5% |
| Cyclohexadimethylsiloxane | 5% |
| Ethyl guar with a degree of substitution of approximately 2.5 (N-Hance AG 200 ® from the company Aqualon) | 1% |

The emulsion is prepared in the following way: phases A and B are prepared by simple mixing under warm conditions of the constituents and are homogenized separately with stirring at 70–75° C. The fatty phase B is then dispersed with stirring in the aqueous phase A.

An emulsion is obtained with a smooth and creamy texture.

EXAMPLE 2
Nourishing Cream for Very Dry Skin

| Phase A | |
|---|---|
| Crosslinked poly(2-acrylamido-2-methyl-propanesulphonic acid) (Example A of EP 815,844), at 2% in water | 1% |
| Glycerol | 5% |
| Preservatives | 0.3% |
| Water | q.s. for 100% |
| Phase B | |
| Soybean oil | 20% |
| Triglycerides of caprylic/capric acids | 5% |
| Cyclohexadimethylsiloxane | 5% |
| Ethyl guar (N-Hance AG 50 ® from the company Aqualon) | 1.5% |

The emulsion is prepared according to Example 1. A cream with a dry texture on application is obtained, contributing a soothing effect to the skin.

EXAMPLE 3
Make-up Removing Emulsion for Dry Skin

| Phase A | |
|---|---|
| Crosslinked poly(2-acrylamido-2-methyl-propanesulphonic acid) (Example A of EP 815,844), at 2% in water | 1% |
| Preservatives | 0.3% |
| Water | q.s. for 100% |
| Phase B | |
| Isopropyl palmitate | 10% |
| Octyl octanoate | 10% |
| Ethyl guar (N-Hance AG 50 ® from the company Aqualon) | 1% |

The emulsion is prepared according to Example 1. A supple emulsion is obtained which spreads easily over the skin and which exhibits a very good make-up removing power.

EXAMPLE 4

The following emulsions A and B are compared under the microscope:

| Emulsion A: | |
|---|---|
| Phase A | |
| Crosslinked poly(2-acrylamido-2-methyl-propanesulphonic acid) (Example A of EP 815,844), at 2% in water | 1.5% |
| Preservatives | 0.3% |
| Water | q.s. for 100% |
| Phase B | |
| Ethyl guar (N-Hance AG 50 ® from the company Aqualon) | 0.8% |
| Triglycerides of caprylic/capric acids | 19.2% |
| Emulsion B: | |
| Phase A | |
| Crosslinked poly(2-acrylamido-2-methyl-propanesulphonic acid) (Example A of EP 815,844), at 2% in water | 1.5% |
| Preservatives | 0.3% |
| Water | q.s. for 100% |
| Phase B | |
| Triglycerides of caprylic/capric acids | 20% |

The following results are obtained:

Emulsion A is fine and even and the edges are sharp. After storing at 20° C. for 18 months, it is still stable.

Emulsion B is unstable and rapidly "phase separates", on the very day of its manufacture.

What is claimed is:

1. An emulsion composition, comprising:
   an aqueous phase;
   a fatty phase,
   at least one hydrophilic thickening compound, and
   at least one polysaccharide alkyl ether formed of two units containing at least two different oside rings, each of said two units containing at least one hydroxyl group substituted by a saturated hydrocarbon-containing chain, and
   at least one solvent for said at least one polysaccharide alkyl ether.

2. The emulsion composition according to claim 1, wherein said at least one hydrophilic thickening compound is chosen from synthetic polymers, polysaccharide biopolymers, aluminium magnesium silicates, and inorganic thickeners.

3. The emulsion composition according to claim 2, wherein said polysaccharide biopolymers are chosen from xanthan gum, locust bean gum, guar gum, alginates, and modified celluloses.

4. The emulsion composition according to claim 3, wherein said modified celluloses are chosen from hydroxyethylcellulose, methylcellulose, hydroxypropylcellulose, and carboxymethylcellulose.

5. The emulsion composition according to claim 2, wherein said inorganic thickeners are chosen from smectites and hectorites, which may be modified or unmodified.

6. The emulsion composition according to claim 1, wherein said at least one hydrophilic thickening compound is chosen from:
  polyacrylic acids; acrylic acid homopolymers and copolymers, which may or may not be crosslinked, and salts thereof;
  polyacrylamide-based polymers; and
  copolymers which may or may not be crosslinked, containing:
    a major fraction of monomeric units originating from monomers chosen from mono-olefinically unsaturated $C_3$–$C_6$ carboxylic acid monomers and of mono-olefinically unsaturated $C_3$–$C_6$ carboxylic anhydride, and
    a minor fraction of monomeric units originating from monomers chosen from esters with a fatty chain of acrylic acid monomer.

7. The emulsion composition according to claim 6, wherein said polyacrylic acids are chosen from poly (glyceryl(meth)acrylate) polymers.

8. The emulsion composition according to claim 6, wherein said polyacrylamide-based polymers are chosen from:
  oil-in-water emulsions comprising from 35 to 45% by weight of crosslinked neutralized acrylamide/2-acrylamido-2-methylpropanesulphonic acid copolymers, from 15 to 25% by weight of isoparaffin hydrocarbons, from 3 to 8% by weight of polyethylene glycol 7EO lauryl ether, and water;
  acrylate/octylacrylamide copolymers;
  crosslinked polymers of methacryloyloxyethyltrimethylammonium chloride and of acrylamide;
  crosslinked polymers of acrylamide and of ammonium acrylate; and
  crosslinked poly(2-acrylamido-2-methylpropanesulphonic acid) polymers which may be substantially or completely neutralized.

9. The emulsion composition according to claim 1, wherein said at least one hydrophilic thickening compound is chosen from:
  crosslinked poly(2-acrylamido-2-methyl-propanesulphonic acid) polymers which may be substantially or completely neutralized, containing randomly distributed:
    units of formula (1):

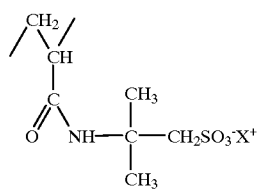

(1)

in which:

$X^+$ is chosen from cations, wherein not more than 10 mol % of said cations are $H^+$ protons, and further wherein said unit of formula (1) is present in an amount ranging from 90 to 99.9% by weight of said crosslinked poly(2-acrylamido-2-methyl-propanesulphonic acid) polymers; and crosslinking units produced from at least one monomer having at least two olefinic double bonds, wherein said crosslinking units are present in an amount ranging from 0.01 to 10% by weight of said crosslinked poly(2-acrylamido-2-methyl-propanesulphonic acid) polymers.

10. The emulsion composition according to claim 1, wherein said at least one hydrophilic thickening compound is chosen from acrylate/$C_{10}$–$C_{30}$ alkyl acrylate copolymers.

11. The emulsion composition according to claim 1, wherein said at least one hydrophilic thickening compound is present an amount ranging from 0.05 to 10% by weight with respect to the total weight of said emulsion composition.

12. The emulsion composition according to claim 11, wherein said amount ranges from 0.5 to 4%.

13. The emulsion composition according to claim 1, wherein said saturated hydrocarbon-containing chain of said polysaccharide alkyl ether contains from 1 to 24 carbon atoms.

14. The emulsion composition according to claim 13, wherein said saturated hydrocarbon-containing chain of said polysaccharide alkyl ether contains from 1 to 10 carbon atoms.

15. The emulsion composition according to claim 14, wherein said saturated hydrocarbon-containing chain of said polysaccharide alkyl ether contains from 1 to 6 carbon atoms.

16. The emulsion composition according to claim 15, wherein said saturated hydrocarbon-containing chain of said polysaccharide alkyl ether contains from 1 to 3 carbon atoms.

17. The emulsion composition according to claim 1, wherein said at least one polysaccharide alkyl ether has a weight-average molecular weight of greater than 100,000.

18. The emulsion composition according to claim 17, wherein said at least one polysaccharide alkyl ether has a weight-average molecular weight of greater than 200,000.

19. The emulsion composition according to claim 1, wherein said at least one polysaccharide alkyl ether contains from one to six hydroxyl groups per unit, and further wherein said hydroxyl groups are substituted by a saturated hydrocarbon-containing chain.

20. The emulsion composition according to claim 19, wherein said at least one polysaccharide alkyl ether contains from two to four hydroxyl groups per unit, and further wherein said hydroxyl groups are substituted by a saturated hydrocarbon-containing chain.

21. The emulsion composition according to claim 1, wherein said at least one polysaccharide alkyl ether is chosen from alkyl ethers of gums.

22. The emulsion composition according to claim 21, wherein said gum is nonionic overall.

23. The emulsion composition according to claim 22, in which said gum is chosen from; guar gums; locust bean gums; karaya gums; and gum tragacanth.

24. The emulsion composition according claim 1, wherein said at least one polysaccharide alkyl ether is chosen from alkylated galactomannans having an alkyl chain ranging in length from $C_1$ to $C_6$.

25. The emulsion composition according claim 24, wherein said alkyl chain ranges in length from $C_1$ to $C_3$.

26. The emulsion composition according claim 24, wherein said alkyl chain is an ethylated guar having a degree of substitution ranging from 2 to 3.

27. The emulsion composition according claim 26, wherein said degree of substitution ranges from 2.5 to 2.9.

28. The emulsion composition according to claim 1, wherein said at least one polysaccharide alkyl ether is present in an amount ranging from 0.1 to 10% by weight relative to the total weight of said emulsion composition.

29. The emulsion composition according to claim 28, wherein said amount ranges from 0.5 to 2%.

30. The emulsion composition according to claim 1, wherein said at least one solvent medium for said at least one polysaccharide alkyl ether comprises:
    oils having an origin chosen from vegetable, animal, mineral, and synthetic origins.

31. The emulsion composition according to claim 30, wherein said oils are liquid triglycerides having an origin chosen from vegetables.

32. The emulsion composition according to claim 30, wherein said oils are triglycerides of caprylic/capric acids having an origin chosen from vegetables.

33. The emulsion composition according to claim 30, wherein said oils are liquid lanolin having an origin chosen from animals.

34. The emulsion composition according to claim 30, wherein said oils are chosen from fatty alcohols, esters and phenylated silicones having an origin chosen from synthetic origins.

35. The emulsion composition according to claim 34, wherein said oils are chosen from:
    2-octyldodecanol as a fatty alcohol,
    fatty acid esters as an ester, and
    phenyl trimethicones, diphenyl dimethicones and polymethylphenylsiloxanes as a phenylated silicone.

36. The emulsion composition according to claim 35, wherein said fatty acid esters have a total number of carbon atoms ranging from 12 to 80.

37. The emulsion composition according to claim 36, wherein said total number of carbon atoms ranges from 16 to 50.

38. The emulsion composition according to claim 1, wherein said at least one solvent medium for said at least one polysaccharide alkyl ether is present in an amount ranging from 15 to 99.9% by weight of the total weight of the oily phase of the emulsion.

39. The emulsion composition according to claim 38, wherein said amount ranges from 75 to 95%.

40. The emulsion composition according to claim 1, wherein said emulsion composition has a form of an oil-in-water emulsion comprising an internal fatty or oily phase dispersed in an external aqueous phase.

41. The emulsion composition according to claim 1, wherein said emulsion composition does not comprise a surfactant.

42. A cosmetic or dermatological product, comprising an emulsion composition comprising:
    an aqueous phase;
    a fatty phase;
    at least one hydrophilic thickening compound; and
    at least one polysaccharide alkyl ether formed of two units containing at least two different oside rings, each of said two units containing at least one hydroxyl group substituted by a saturated hydrocarbon-containing chain; and
    at least one solvent for said at least one polysaccharide alkyl ether.

43. The cosmetic or dermatological product according to claim 42, wherein said emulsion composition is present in an amount effective for the cosmetic or dermatological treatment of skin, hair, eyelashes, eyebrows, nails, mucous membranes or scalp.

44. The cosmetic or dermatological product according to claim 42, wherein said product is for caring for the face or body, making up the face or body, removing make-up, or antisun protection.

45. A process for making a dermatological composition for treatment of skin, hair, eyelashes, eyebrows, nails, scalp, or mucous membranes, the step of forming said dermatological composition and including therein an emulsion composition, comprising:
    an aqueous phase;
    a fatty phase;
    at least one hydrophilic thickening compound; and
    at least one polysaccharide alkyl ether formed of two units containing at least two different oside rings, each of said two units containing at least one hydroxyl group substituted by a saturated hydrocarbon-containing chain; and
    at least one solvent for said at least one polysaccharide alkyl ether.

46. A cosmetic or dermatological composition for dry or sensitive skin comprising an emulsion comprising:
    an aqueous phase;
    a fatty phase,
    at least one hydrophilic thickening compound, and
    at least one polysaccharide alkyl ether formed of two units containing at least two different oside rings, each of said two units containing at least one hydroxyl group substituted by a saturated hydrocarbon-containing chain, and
    at least one solvent for said at least one polysaccharide alkyl ether.

47. A process for a nontherapeutic treatment of the skin, hair, eyelashes, eyebrows, nails, mucous membranes or scalp, comprising applying to said skin, hair, eyelashes, eyebrows, nails, mucous membranes; or scalp an emulsion comprising:
    an aqueous phase;
    an oily phase;
    at least one hydrophilic thickening compound, and
    at least one polysaccharide alkyl ether formed of two units containing at least two different oside rings, each of said two units contains at least one hydroxyl group substituted by a saturated hydrocarbon-containing chain, and
    wherein said emulsion comprises at least one solvent for said at least one polysaccharide alkyl ether.

48. A process for a nontherapeutic treatment of dry or sensitive skin, comprising applying to said skin emulsion comprising:
    an aqueous phase;
    an oily phase;
    at least one hydrophilic thickening compound, and
    at least one polysaccharide alkyl ether formed of two units containing at least two different oside rings, each of said two units contains at least one hydroxyl group substituted by a saturated hydrocarbon-containing chain, and
    wherein said emulsion comprises at least one solvent for said at least one polysaccharide alkyl ether.

49. A method of stabilizing an emulsion comprising an aqueous phase and an oily phase, comprising including in said emulsion:

at least one hydrophilic thickening compound, and at least one polysaccharide alkyl ether formed of two units containing at least two different oside rings, each of said two units contains at least one hydroxyl group substituted by a saturated hydrocarbon-containing chain, and wherein said emulsion comprises at least one solvent for said at least one polysaccharide alkyl ether.

50. The process according to claim 49, wherein said emulsion is an oil-in-water emulsion composition.

51. The method according to claim 49, wherein said emulsion does not comprise a surfactant.

52. The emulsion composition according to claim 31, wherein said vegetables are chosen from sunflowers, maizes, soybeans, jojobas, cucumbers, grape seeds, sesames, hazelnuts, apricots, macadamias, and castor oils.

* * * * *